United States Patent [19]
Herzog

[11] Patent Number: 5,867,856
[45] Date of Patent: Feb. 9, 1999

[54] BRUSH SECTION FOR AN ELECTRIC TOOTHBRUSH

[75] Inventor: Karl Herzog, Frankfurt, Germany

[73] Assignee: Braun Aktiengesellschaft, Frankfurt, Germany

[21] Appl. No.: 811,524

[22] Filed: Mar. 4, 1997

[30] Foreign Application Priority Data

Sep. 23, 1994 [DE] Germany .......................... 44 33 914.3

[51] Int. Cl.$^6$ .................................................. A46B 13/02
[52] U.S. Cl. .................................................. 15/22.4; 15/28
[58] Field of Search .................................... 15/22.1, 22.4, 15/23, 24, 28, 29

[56] References Cited

U.S. PATENT DOCUMENTS

| | | | |
|---|---|---|---|
| 4,179,765 | 12/1979 | Teague et al. | 15/22.1 |
| 5,383,242 | 1/1995 | Bigler et al. | 15/22.1 |
| 5,461,744 | 10/1995 | Merbach | 15/22.1 |
| 5,504,959 | 4/1996 | Yukawa et al. | 15/22.1 |
| 5,524,312 | 6/1996 | Tan et al. | 15/22.1 |
| 5,577,285 | 11/1996 | Drossler | 15/22.1 |
| 5,732,433 | 3/1998 | Gocking et al. | 15/28 |

FOREIGN PATENT DOCUMENTS

| | | |
|---|---|---|
| A 39 31 982 | 4/1991 | Germany . |
| A 39 37 850 | 5/1991 | Germany . |
| U 93 04 184 | 5/1993 | Germany . |
| A 42 39 251 | 5/1994 | Germany . |
| WO A 94 12121 | 6/1994 | WIPO . |

OTHER PUBLICATIONS

Copy of International Search Report dated Nov. 29, 1995.

*Primary Examiner*—Terrence Till
*Attorney, Agent, or Firm*—Fish & Richardson P.C.

[57] ABSTRACT

The invention is directed to a brush section (1) for an electric toothbrush which includes a mounting tube (2) in which a shaft (7) is received which is mounted so as to be rotary about a longitudinal axis (3) and is adapted to be driven in an oscillatory fashion. Further, the brush section (1) includes a bristle supporting structure (11) which is arranged so as to be rotary about a transverse axis (14) by means of a bearing pin (18) and is adapted to be set in a rotational motion (29) about said transverse axis (14) by means of a drive pin (24). The fixed connection between the bearing pin (18) and the shaft (7) has the added effect of causing the bristle supporting structure (11) to perform a pivotal motion (28) about the longitudinal axis (3). The rotational motion (29) of the bristle supporting structure (11) produces a cleaning action on a user's exposed tooth surfaces, whilst the pivotal motion (28) acts to accomplish an additional cleansing operation on the user's inter-proximal surfaces.

13 Claims, 4 Drawing Sheets

BRUSH SECTION FOR AN ELECTRIC TOOTHBRUSH

This is a continuation of application Ser. No. PCT/EP95/03223, filed Aug. 16, 1995, which claims priority from German Application P 44 22 914.3, filed Sept. 23, 1994.

BACKGROUND OF THE INVENTION

This invention relates very generally to electric toothbrushes and particularly to a brush section for an electric toothbrush.

A brush section of this type is known from German Offenlegungsschrift DE 39 37 850 A1 which is hereby incorporated in the disclosure content of the present patent application by express reference. In this specification, an electric toothbrush is described which has a handle section from which a drive shaft projects outwardly. The handle section receives in its interior electric drive means with the aid of which the drive shaft can be set in an oscillatory rotational motion about its longitudinal axis. A brush section extending in the direction of the longitudinal axis and having a mounting tube with a bristle supporting structure arranged at its end is adapted to be push-fitted onto the handle section and the drive shaft. The mounting tube accommodates therein a shaft which, when push-fitted, is coupled to the drive shaft. Extending from the bristle supporting structure are bristles which are arranged approximately transversely to the longitudinal axis of the brush section. By means of a bevel gear arrangement, the oscillatory rotational motion transmitted by the drive shaft to the shaft of the brush section is deflected by about 90 degrees. As a result, with the electric toothbrush activated, the bristle supporting structure executes an oscillatory rotational motion about an axis which is approximately transverse to the longitudinal axis of the brush section and thus approximately parallel to the bristles. The cleansing face formed by the free ends of the bristles thus performs an oscillatory rotational motion on a user's tooth surfaces. This oscillatory rotational motion is apt to produce a good cleaning action on the tooth surfaces.

BRIEF SUMMARY OF THE INVENTION

It is an object of the present invention to provide a brush section for an electric toothbrush with which an improved dental cleaning operation, in particular with regard to the cleaning of interproximal surfaces, can be accomplished.

According to the present invention, this object is accomplished in a brush section with means provided which effect an additional pivotal motion of the bristle supporting structure about the longitudinal axis.

As a result of the additional pivotal motion of the bristle supporting structure about the longitudinal axis, the cleansing face formed by the free ends of the bristles executes an oscillatory pivotal motion in addition to the oscillatory rotational motion. The rotational motion provides good cleaning of a user's tooth surfaces as heretofore. By means of the pivotal motion of the cleansing face, an improved dental cleaning action is possible by reason of the additional component of motion. In particular with the customary alignment of the brush section by its user, that is, the positioning of the cleansing face of the brush section against the buccal and lingual tooth surfaces, the pivotal motion proceeds approximately parallel to the interproximal surfaces so that a materially improved cleaning operation can be accomplished on the user's interproximal surfaces. Improved cleaning of the teeth and in particular of the interproximal surfaces is thus effected without additional action on the user's part, that is, automatically, which is conducive to application by, and comfort for, the user. This additional pivotal motion about the longitudinal axis could also be referred to as an oscillatory pivotal motion, with a drive pin forming a fixed point for the bristle supporting structure.

In an advantageous aspect of the present invention, the bearing pin executes a pivotal motion about the longitudinal axis on account of its fixed connection with the shaft. Further, because the bristle supporting structure is mounted on the bearing pin, the bristle supporting structure performs equally this pivotal motion. In this manner, a straightforward and in particular economical possibility is available to accomplish the additional pivotal motion of the bristle supporting structure about the longitudinal axis. Conveniently, the bearing pin is a press-fit within a bore in the shaft. This facilitates the manufacture of the brush section still further.

In an advantageous further aspect of the present invention, the bristle supporting structure is rotatably mounted on the bearing pin by means of a blind-end bore. To prevent the bristle supporting structure from falling off from the bearing pin, the bristle supporting structure is coupled with the shaft. A particularly suitable coupling possibility is one in which the shaft extending into the bridge-shaped opening prevents the bristle supporting structure from falling out. It will be understood, of course, that the bristle supporting structure may be held on the bearing pin in other ways using, for example, cotter pins or the like. The embodiments claimed represent, however, particularly simple and economical possibilities of mounting the bristle supporting structure on the bearing pin, in particular with a view to manufacturing the brush section.

By coupling the bristle supporting structure with the mounting tube in accordance with another aspect of the present invention, the bristle supporting structure is prevented from rotating freely about the bearing pin. Instead, this coupling has the effect of producing the oscillatory pivotal motion of the bristle supporting structure while creating at the same time the oscillatory rotational motion of the bristle supporting structure. By coupling the bristle supporting structure with the mounting tube in this manner, the heretofore rotational motion of the cleansing face is accomplished in a simple manner.

In an advantageous further aspect of the present invention, the above-referenced coupling arrangement is accomplished by having a drive pin which projects away from the mounting tube extend into an opening in the bristle supporting structure. It will be understood that the coupling arrangement may also be realized in different ways using, for example, meshing teeth or the like. However, the further aspect as claimed represents a very simple and low-cost possibility of implementing the desired coupling. Conveniently, the drive pin is a press-fit within a bore in the mounting tube. This facilitates in particular the manufacture of the brush section still further. Moreover, it is particularly advantageous to configure the opening in the bristle supporting structure in accordance with the features of patent claim 9. The shape of the opening and/or the selection of a wear-resistant material result in reduced wear, thus prolonging the service life of the brush section.

Some possibilities for how the bearing pin and the drive pin may be arranged relative to each other in order to accomplish an additional nutating motion of the bristle supporting structure and thus of the cleansing face are as follows. The bearing pin and the shaft can be arranged at a relative angle of about 70 degrees to about 110 degrees. The drive pin and the shaft can be arranged at a relative angle of about 60 degrees to about 120 degrees. The bearing pin and the drive pin can be arranged at a relative angle of about 0 degrees to about 20 degrees. These angular ranges have proven to be particularly advantageous in practice.

The invention is suitable for implementation not only in the form of the brush section as such, but also in the form of an electric toothbrush to which a corresponding brush section is attached such as, for example, by push-fitting.

Further features, advantages and application possibilities of the present invention will become apparent from the subsequent description of embodiments illustrated in more detail in the accompanying drawings. It will be understood that any single feature and any combination of single features described and/or represented by illustration form the subject-matter of the present invention, irrespective of their summary in the claims and their back-reference.

DETAILED DESCRIPTION OF THE PREFERRED EMBODIMENTS

The brush sections described in the following with reference to FIGS. 1 to 4 are suited to operate in conjunction with an electric toothbrush of the type described in German Offenlegungsschrift DE 39 37 850 A1 and hereby incorporated in the disclosure content of the present patent application by express reference. This electric toothbrush includes a handle section from which a drive shaft projects outwardly. The handle section accommodates in its interior electric drive means imparting an oscillatory rotational motion to the drive shaft about its longitudinal axis when activated. The range of the rotation angle swept during this motion is ±35 degrees, approximately. The drive shaft and that end of the handle section from which the drive shaft projects have their outer surfaces contoured for push-fitting engagement with a brush section and for transmission of the rotary motion produced.

Figure 1:
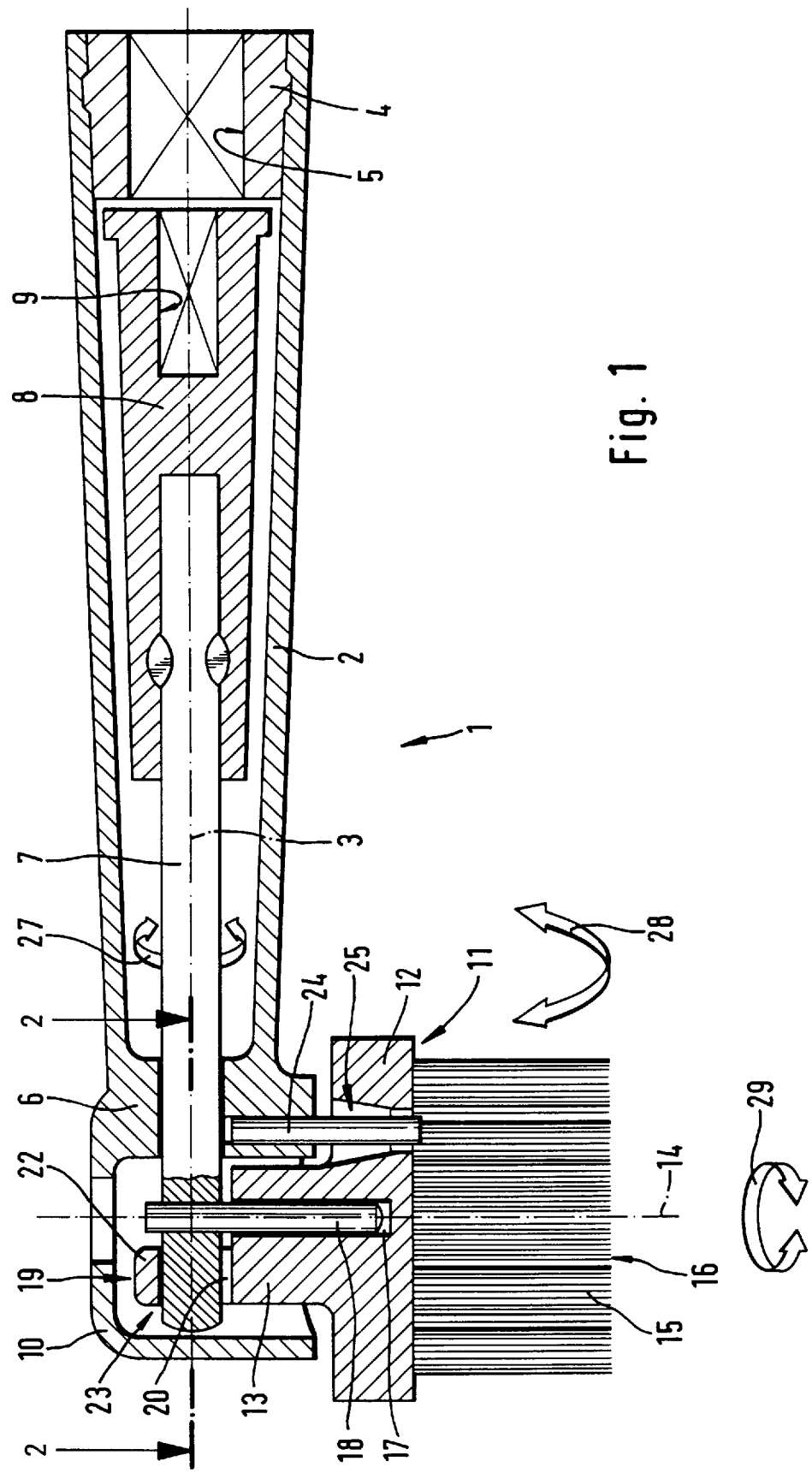
FIG. 1 is a schematic longitudinal sectional view of a brush section for an electric toothbrush illustrating a first embodiment thereof.
Figure 1A:
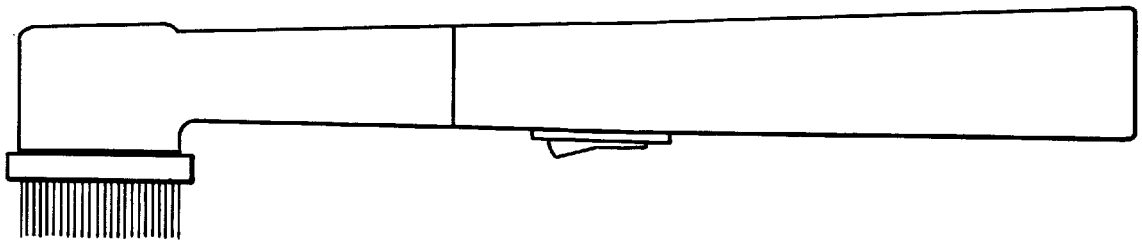
FIG. 1A shows an electric toothbrush having a handle section and a brush section.
Figure 2:
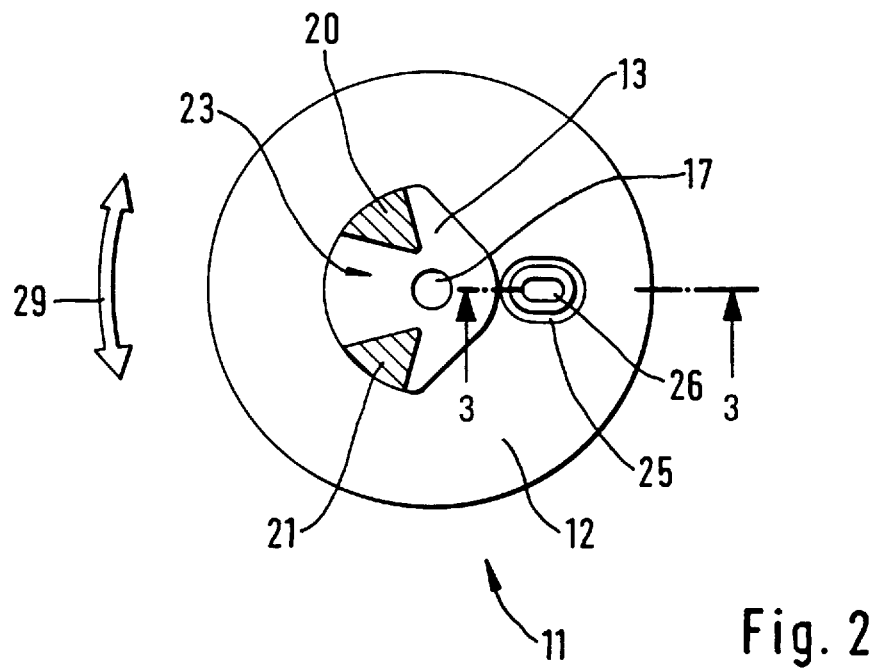
FIG. 2 is a schematic cross sectional view of the bristle supporting structure of the brush section of FIG. 1, taken along the plane 2—2 of FIG. 1.
Figure 3:
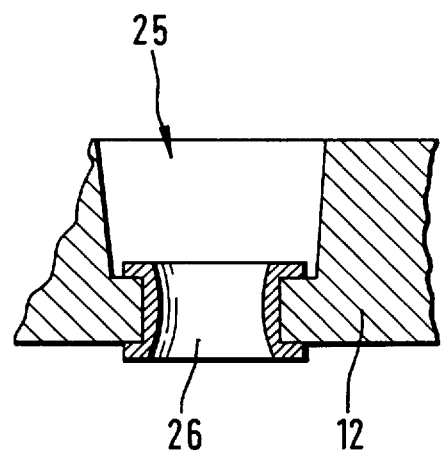
FIG. 3 is a schematic partial longitudinal sectional view of the bristle supporting structure of the brush section of FIG. 1, taken along the plane 3—3 of FIG. 2.

FIGS. 1 to 3 illustrate a brush section 1 which may be push-fitted onto the handle section and the drive shaft of the electric toothbrush referred to in the foregoing. The brush section 1 includes a mounting tube 2 extending in the direction of a longitudinal axis 3. At its free end close to the handle section, the mounting tube 2 has a profile ring 4 with an inside contour 5 complementary with the outside contour of the handle section. In this manner, the brush section 1 can be push-fitted onto the handle section in a manner preventing relative rotation.

At its end remote from the handle section, the mounting tube 2 has a bearing 6 in which a shaft 7 is carried so as to be rotatable. The shaft 7 is arranged in the longitudinal axis 3 of the mounting tube 2 and is preferably made of metal. The shaft 7 extends from the bearing 6 in the direction close to the handle section approximately up to the center of the mounting tube 2, while projecting in the direction remote from the handle section beyond the bearing 6 and thus beyond the mounting tube 2 by a small amount. In the direction close to the handle section, the shaft 7 is fixedly coupled to another shaft 8 arranged in the longitudinal axis 3 and preferably fabricated from a plastic. The second shaft 8 has at its free end close to the handle section an inside contour 9 complementary with the outside contour of the drive shaft projecting outwardly from the handle section. This enables the drive shaft to be coupled to the second shaft 8 and thus also to the shaft 7 in a manner preventing relative rotation.

The inside and outside contours 5, 9 may be of a square, stellate or similar configuration when viewed in cross section, which are conformed to each other such as to enable a user to push and pull the brush section 1 onto and, respectively, off the handle section with ease, while at the same time a secure seat of the brush section 1 on the handle section is ensured.

At its end remote from the handle section, the mounting tube 2 has a cap structure 10 covering approximately the area by which the shaft 7 projects beyond the bearing 6 and thus beyond the mounting tube 2. Further arranged in this area are a bristle supporting structure 11 as well as means for coupling the bristle supporting structure 11 to the shaft 7 and to the mounting tube 2.

The bristle supporting structure 11 includes a disk-shaped plate 12 and a hub 13 and is essentially rotationally symmetrical to a transverse axis 14 disposed at an angle of about 90 degrees to the longitudinal axis 3. On its side facing away from the shaft 7, the plate 12 has a plurality of bristles 15 extending from the plate 12 in a direction approximately parallel to the transverse axis 14. The bristles 15 are all of about equal length so that their free ends form an approximately circular cleansing face 16 extending approximately parallel to the longitudinal axis 3. It will be understood, of course, that cleansing faces 16 of a completely different appearance may be provided without limiting the invention, including, for example, cleansing faces which are profiled and/or inclined relative to the longitudinal axis 3 by providing the bristles 15 with different lengths. The hub 13 which includes a blind-end bore 17 therein is disposed on the side of the plate 12 close to the shaft 7. The blind-end bore 17 is in concentric alignment with the transverse axis 14, pointing approximately at the center of the cleansing face 16.

In the section of the shaft 7 projecting into the area of the cap structure 10, a bearing pin 18 is press-fitted into a corresponding bore of the shaft 7 concentrically with the transverse axis 14. Bearing pin 18 and blind-end bore 17 are conformed to each other in respect of length and diameter such as to provide in combination a bearing for the bristle supporting structure 11. As a result, the bristle supporting structure 11 is mounted rotatably about the bearing pin 18 and thus about the transverse axis 14.

In the area of the cap structure 10 at the location of the free end of the shaft 7, the bristle supporting structure 11 has a bridge 19 composed of two piers 20, 21 and one beam 22. These components form an opening 23 which extends approximately in the direction of the longitudinal axis 3 and whose cross section is somewhat larger than the cross section of the shaft 7. The free end of the shaft 7 is passed through the opening 23 without making contact with the bridge 19 and thus the bristle supporting structure 11. This arrangement prevents the bristle supporting structure 11 from slipping on the bearing pin 18 or, which is worse, falling out. The opening 23 and the piers 20, 21 become particularly apparent from FIG. 2.

In the area of the bearing 6 on the side of the mounting tube 2 close to the plate 12 of the bristle supporting structure 11, a drive pin 24 is press-fitted within a corresponding bore in the mounting tube 2. The penetration depth of the drive pin 24 in the mounting tube 2 is selected so small that there is no contact with the shaft 7. Further, the drive pin 24 extends approximately parallel to the transverse axis 14.

An opening 25 into which the drive pin 24 projects is provided in the plate 12 of the bristle supporting structure 11. This opening 25 is aligned approximately parallel to the transverse axis 14, with a cross section approximately in the shape of an elongated hole. The opening 25 may be lined with a bushing 26 made of a wear-resistant material such as, for example, metal, ceramics, rubber or the like. The opening 25 and the bushing 26 become apparent in particular from FIGS. 2 and 3.

When the electric toothbrush is turned on, the drive shaft projecting outwardly from the handle section imparts an oscillatory rotational motion 27 about the longitudinal axis 3 to the shaft 7 of the brush section 1 push-fitted to the handle section. In consequence, the bearing pin 18 executes an oscillatory pivotal motion, equally about the longitudinal axis 3. As a result of the mounting arrangement of the bristle supporting structure 11 on the bearing pin 18, the bristle supporting structure 11 and thus also the cleansing face 16 are set in an oscillatory pivotal motion 28 about the longitudinal axis 3. The oscillatory pivotal motion 28 is substantially identical with the oscillatory rotational motion 27. This means that the cleansing face 16 performs approximately an up and down and/or a reciprocating motion in which the cleansing face 16 moves at all times on a shell surface of an imaginary cylinder about the longitudinal axis 3.

The drive pin 24 has the effect of maintaining the position of the opening 25 of the bristle supporting structure 11 relative to the mounting tube 2 essentially unchanged. As a result, the oscillatory pivotal motion 28 of the bristle supporting structure 11 is only possible if the bristle supporting structure 11 performs at the same time an oscillatory rotational motion 29 about the transverse axis 14 provided by the bearing pin 18. This means that the cleansing face 16 performs equally this oscillatory rotational motion 29 about the transverse axis 14.

The oscillatory pivotal motion 28 and the oscillatory rotational motion 29 of the bristle supporting structure 11 and thus of the cleansing face 16 are additive to result in a movement in which the cleansing face 16 is at the same time pivoted and rotated.

In the use of the described electric toothbrush with the brush section 1 for dental cleaning in which a user, as is customary practice, guides the cleansing face 16 of the brush section 1 approximately parallel to the mouth along the tooth surfaces, the oscillatory rotational motion 29 of the cleansing face 16 performs a cleaning function on in particular the exposed tooth surfaces, that is, the buccal and lingual surfaces of the teeth. By means of the oscillatory pivotal motion 28 of the cleansing face 16, the user accomplishes an added cleaning operation on in particular the interproximal surfaces, that is, the not freely accessible tooth surfaces between individual teeth.

Figure 4:
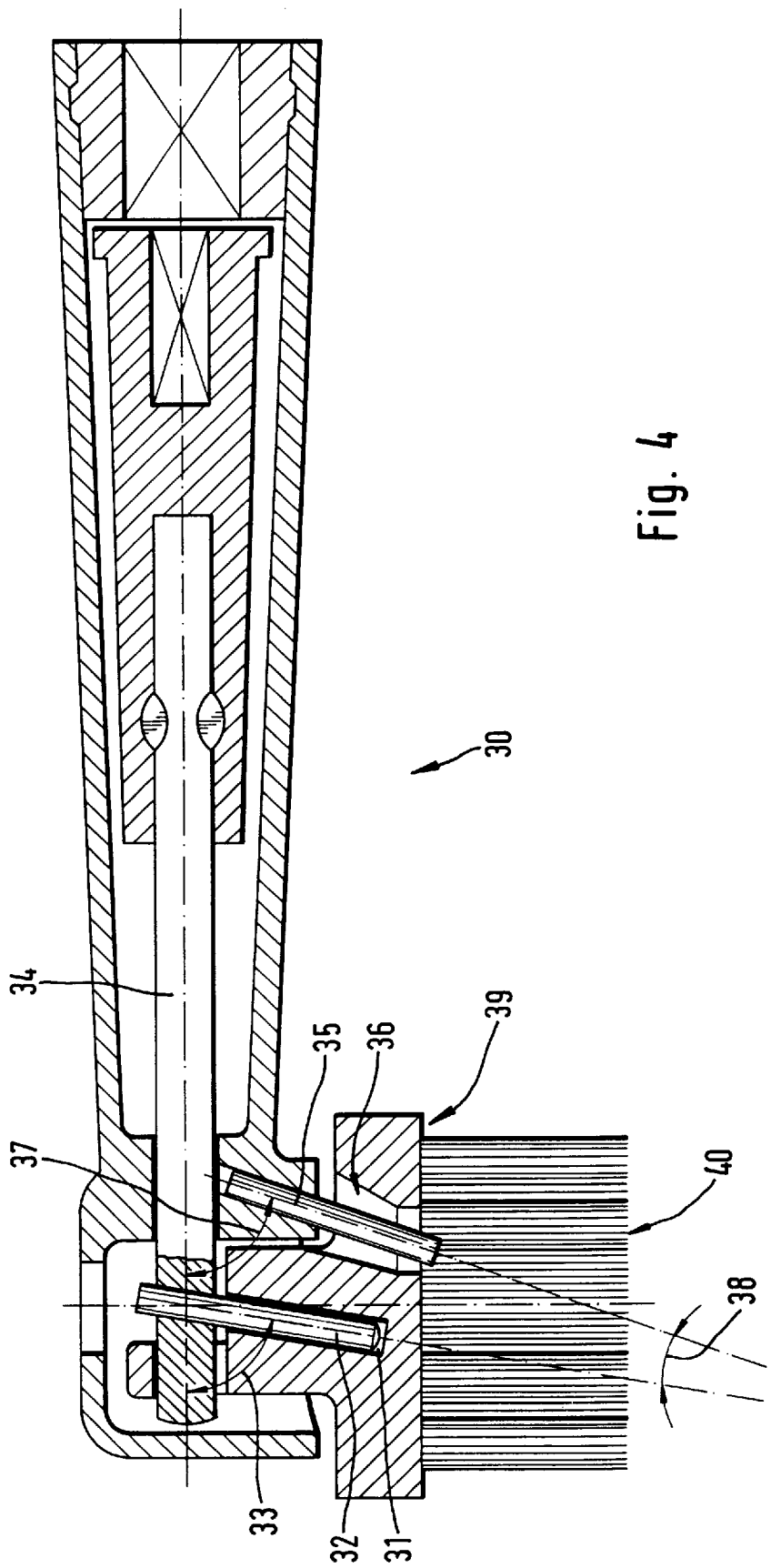
FIG. 4 is a schematic longitudinal sectional view of a brush section for an electric toothbrush illustrating a second embodiment thereof.

The brush section 30 illustrated in FIG. 4 corresponds essentially to the brush section 1 shown in FIGS. 1 to 3, with the exception of the arrangement of the blind-end bore 17, the bearing pin 18, the drive pin 24 and the opening 25. In the brush section 30 shown in FIG. 4, a blind-end bore 31 and a bearing pin 32 are provided which are arranged at an angle 33 to a shaft 34 which is in the range of about 70 degrees to about 110 degrees, in particular of about 80 degrees or 100 degrees. Further, the brush section 30 of FIG. 4 includes a drive pin 35 and an opening 36 disposed at an angle 37 to the shaft 34 which is in the range of about 60 degrees to about 120 degrees, in particular of about 75 degrees. From this arrangement, further angular ranges may result for the angle 38 between the blind-end bore 31 or the bearing pin 32 and the drive pin 35 or the opening 36, preferred angles being in the range of about 0 to about 20 degrees, in particular of about 10 degrees. By suitably selecting the angles 33, 37 and 38, an additional nutating motion of a bristle supporting structure 39 and thus of a cleansing face 40 is accomplished.

The invention claimed is:

1. A brush section for an electric toothbrush, comprising:
   a shaft;
   a mounting tube in which the shaft is received and is mounted so as to be rotary about a longitudinal axis;
   a bristle supporting structure which is arranged so as to be rotary about a transverse axis and is coupled to the shaft such that a rotational motion of the shaft about the longitudinal axis effects a rotational motion of the bristle supporting structure about the transverse axis (; and
   a coupling mechanism which effects an additional pivotal motion of the bristle supporting structure about the longitudinal axis.

2. The brush section as claimed in patent claim 1, wherein the coupling mechanism includes a bearing pin arranged along the transverse axis, projecting outwardly from the shaft, and carrying rotatably thereon the bristle supporting structure.

3. The brush section as claimed in patent claim 2, in which the bearing pin and the shaft are arranged at a relative angle of about 90 degrees.

4. The brush section as claimed in patent claim 2, in which the bearing pin and the shaft are arranged at a relative angle of about 70 degrees to about 110 degrees.

5. The brush section as claimed in claim 2, wherein the bristle, supporting structure includes a blind-end bore receiving therein the bearing pin, and wherein the brush section further comprises coupling structure which couples the bristle supporting structure with the shaft.

6. The brush section as claimed in claim 1 wherein the bristle supporting structure includes a bridge-type opening into which the shaft extends.

7. The brush section as claimed in claim 1 wherein the bristle supporting structure is coupled with the mounting tube.

8. The brush section as claimed in claim 1 wherein the coupling mechanism includes a drive pin extending, into an opening in the bristle supporting structure and projecting outwardly from the mounting tube.

9. An electric toothbrush as claimed in claim 8 further comprising a bushing in an elongated hole and wherein said bushing defines said opening and is made of a material selected from then group consisting of metal, ceramics, and rubber.

10. The brush section as claimed in claim 8 wherein the drive pin and the shaft are arranged at a relative angle of about 60 degrees to about 120 degrees.

11. The brush section as claimed in claim 8 wherein the opening is an elongated hole.

12. The brush section as claimed in claim 8 wherein the bearing pin and the drive pin are arranged at a relative angle of about 0 degrees to about 20 degrees.

13. An electric toothbrush with the brush section of claim 1, wherein said brush section is adapted to be coupled to said electric toothbrush.

* * * * *